United States Patent [19]

Kiel et al.

[11] Patent Number: 5,011,996
[45] Date of Patent: Apr. 30, 1991

[54] PROCESS FOR THE PREPARATION OF AMINES

[75] Inventors: Wolfgang Kiel, Odenthal; Heinz Ziemann, Leichlingen, both of Fed. Rep. of Germany

[73] Assignee: Bayer Aktiengesellschaft, Leverkusen, Fed. Rep. of Germany

[21] Appl. No.: 375,762

[22] Filed: Jul. 5, 1989

[30] Foreign Application Priority Data

Jul. 20, 1988 [DE] Fed. Rep. of Germany ....... 3824519
Oct. 13, 1988 [DE] Fed. Rep. of Germany ....... 3834848

[51] Int. Cl.$^5$ ................. C07C 209/24; C07C 209/26; C07C 209/28
[52] U.S. Cl. .................................... 564/321; 564/373; 564/374; 564/381; 564/397; 564/398
[58] Field of Search ............... 564/374, 384, 398, 321, 564/373, 375; 514/397

[56] References Cited

U.S. PATENT DOCUMENTS 2,298,284 10/1942 Emerson ............................. 564/397
3,366,684 1/1968 Budd ................................. 564/397 X
3,739,026 6/1973 Wilson, Jr. ......................... 564/397

OTHER PUBLICATIONS

Adams et al., "Organic Reactions", vol. IV., pp. 174–183 (1948).

Primary Examiner—Richard L. Raymond
Attorney, Agent, or Firm—Sprung, Horn, Kramer & Woods

[57] ABSTRACT

Reaction products of oxo compounds and amines or ammonia, in which at least one substituent is aromatic and monosubstituted to trisubstituted by halogen, can be catalytically hydrogenated to the respective amines, the halogen essentially being completely retained if an Ni-containing or Co-containing catalyst is employed and the reaction is carried out in the presence of organic sulphur compounds.

18 Claims, No Drawings

PROCESS FOR THE PREPARATION OF AMINES

BACKGROUND OF THE INVENTION

The invention relates to a process for the preparation of amines in which at least one substient is aromatic and is monosubstituted to trisubstituted by halogen. In this connection, the process starts out from reaction products of oxo compounds and amines or ammonia which carry halogen substituents in the circumstances mentioned. These reaction products are catalytically hydrogenated, an Ni-containing and/or Co-containing catalyst being employed and the reaction being carried out in the presence of organic sulphur compounds.

The catalytic hydrogenation of reaction products of oxo compounds and amines or ammonia is known. Aldehydes and ketones may be mentioned as oxo compounds in accordance with the following scheme:

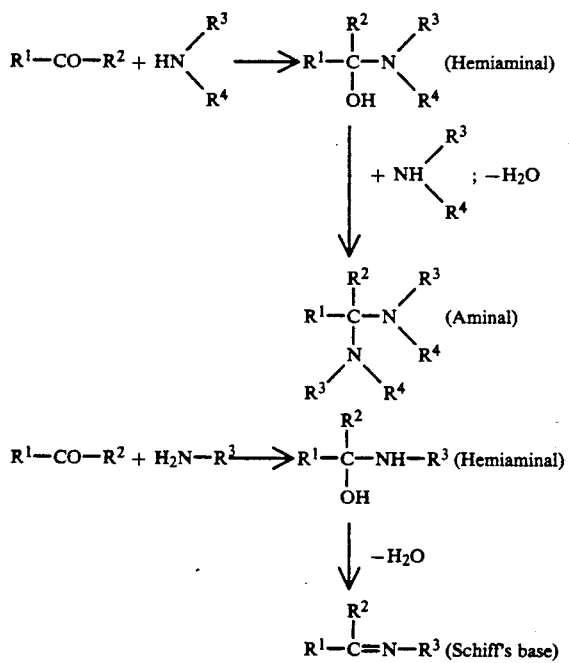

From an aldehyde or ketone and a primary or secondary amine or ammonia, a hemiaminal can therefore first be formed which can react further with a further molecule of the amine or ammonia to give the aminal with the elimination of a molecule of water or (only with primary amines or ammonia) can also react to give the azomethine (Schiff's base, aldimine, ketimine) with the elimination of a molecule of water. Aldimines can additionally be obtained in an indirect manner as reaction products of aldehydes and ammonia by partial hydrogenation of nitriles. All reaction products mentioned (hemiaminal, aminal or azomethine) can be catalytically hydrogenated to give the corresponding amines (Houben-Weyl, Methoden der Organischen Chemie (Methods of Organic Chemistry), 4th edition, volume IV/1c (1980), p. 127/128, 239/240 and 436). Such catalytic hydrogenations should also be possible with the retention of halogen. However, this result is limited to the use of palladium catalysts, and it is further pointed out that the reaction is advantageously carried out at low temperatures and using a deactivated catalyst (page 240). Even using other catalyts, such as platinum or Raney nickel, halogen should be retained (Houben-Weyl, loc. cit.). However, the specific hydrogenations indicated in the references cited do not represent a systematic investigation (page 436, paragraph 3) and in some cases show extremely moderate yields, as in the case of p-chlorobenzyl methyl ketone which can only be converted into the respective amine in 10% of the theoretical yield (Houben-Weyl, bottom of page 436). By-products have to be taken into account, especially in the preparation of strongly basic amines (Houben-Weyl, age 240, paragraph 2).

SUMMARY OF THE INVENTION

It has now surprisingly been found that, for substantial retention of aromatically bonded halogen, the described catalytic hydrogenation on Ni-containing and/or Co-containing catalysts can be carried out if the organic sulphur compounds described below are employed simultaneously.

The invention therefore relates to a process for the preparation of amines of the formula

in which $R^1$, $R^2$ and $R^3$ independently of one another denote hydrogen, straight-chain or branched $C_1$-$C_{12}$-alkyl, $C_3$-$C_8$-cycloalkyl, $C_{12}$-$C_{12}$-aryl or $C_7$-$C_{10}$-aralkyl and $R^4$ represents hydrogen, straight-chain or branched $C_1$-$C_{20}$-alkyl, $C_6$-$C_{12}$-aryl, $C_3$-$C_8$-cycloalkyl or $C_7$-$C_{10}$-aralkyl, where at least one of the radicals $R^1$ to $R^4$ represents aryl or aralkyl which are monosubstituted to trisubstituted by halogen in the aromatic moiety, by catalytic hydrogenation of reaction products of oxo compounds of the formula

and nitrogen compounds of the formula

with the abovementioned meanings for $R^1$ to $R^4$, which is characterized in that an Ni-containing and/or Co-containing catalyst is employed and that the reaction is carried out in the presence of organic sulphur compounds of the formula

in which $R^5$ and $R^6$ independently of one another denote straightchain or branched $C_1$-$C_{12}$-alkyl, hydroxy-$C_2$-$C_{12}$-alkyl, carboxy-$C_1$-$C_{12}$-alkyl or phenyl and furthermore $R^5$ and $R^6$ together may represent —CH═CH—CH═CH—, —(CH$_2$)$_4$—, —(CH$_2$)$_5$—, —(CH$_2$)$_2$—S—(CH$_2$)$_2$— or —(CH$_2$)$_2$—O—(CH$_2$)$_2$—, $R^6$ additionally may denote hydrogen or CO—C-$C_1$-$C_{12}$-alkyl and n assumes the value 0 or 1.

DETAILED DESCRIPTION OF THE INVENTION

Straight-chain or branched $C_1$-$C_1$-alkyl is, for example, methyl, ethyl, propyl, isopropyl, butyl, isobutyl, tert.-butyl, amyl, hexyl, octyl, decyl or dodecyl; $C_1-C_8$-alkyl is preferred, particularly preferably $C_1-C_4$-alkyl. $R^4$ may furthermore also have up to 20 C-atoms and may also be, for example, palmityl, stearyl or eicosyl, Hydroxy-alkyl carries in any position, preferably in the ω-position, a hydroxyl group and may furthermore be interrupted by ether oxygen in the carbon chain. Carboxy-alkyl carries in any position, preferably in the α- or ω-position, a carboxyl group. The same preferred ranges apply as for alkyl.

$C_3-C_8$-Cycloalkyl is, for example, cyclopropyl, cyclobutyl, cyclopentyl, cyclohexyl, cycloheptyl or cyclooctyl, which may be monosubstituted or disubstituted by methyl and/or ethyl. Preferably, cycloalkyl is cyclopropyl, cyclopentyl or cyclohexyl.

$C_8-C_{12}$-Aryl is, for example, phenyl, naphthyl or biphenyl, preferbly phenyl.

$C_7-C_{10}$-Aralkyl is, for example, benzyl, phenylethyl or phenylpropyl, preferbly benzyl and phenylethyl.

At least one of the radicals in the reaction products of oxo compounds with the nitrogen compounds is aryl or aralkyl and is monosubstituted to trisubstituted in the aromatic moiety by halogen, such as fluorine, chlorine or bromine, preferably fluorine or chlorine, particularly preferably chlorine. In the case of multiple substitution, it may also be substitution by different halogen atoms. In a preferred manner, monosubstitution or disubstitution by halogen is present, in a particularly preferred manner monosubstitution by halogen. All aromatic moieties of the radicals may furthermore carry one or two methyl or ethyl groups, methoxy or ethoxy groups, or $C_1-C_4$-dialkylamino groups.

In a preferred manner, oxo compounds of the formula $$R^{11}-CO-R^{12} \qquad (V)$$

are employed in which $R^{11}$ denotes hydrogen, straight-chain or branched $C_1-C_4$-alkyl, $C_3-C_6$-cycloalkyl, phenyl, benzyl or phenylethyl and $R^{12}$ represents hydrogen, straight-chain or branched $C_1-C_4$-alkyl or phenyl.

In a particularly preferred manner, oxo compounds of the formula $$R^{21}-CO-R^{22} \qquad (VI)$$

are employed in which $R^{21}$ denotes hydrogen, straight-chain or branched $C_1-C_4$-alkyl, $C_5-C_6$-cycloalkyl, phenyl, benzyl or phenylethyl and $R^{22}$ represents hydrogen, methyl or ethyl.

In a preferred manner, nitrogen compounds of the formula $$R^{13}-NH-R^{14} \qquad (VII)$$

are furthermore employed in which $R^{13}$ denotes hydrogen, straight-chain or branched $C_1-C_8$-alkyl, $C_3-C_6$-cycloalkyl, phenyl or benzyl and $R^{14}$ represents hydrogen, straight-chain or branched $C_1-C_4$-alkyl or benzyl.

In a particularly preferred form, nitrogen compounds of the formula $$R^{23}-NH-R^{24} \qquad (VIII)$$

are employed in which $R^{23}$ denotes hydrogen, straight-chain or branched $C_1-C_4$-alkyl, $C_5-C_6$-cycloalkyl, phenyl or benzyl and $R^{24}$ represents hydrogen, methyl or ethyl.

In the manner according to the invention, the preferred or particularly preferred oxo compounds or nitrogen compound are also so combined that in their reaction products at least one of the radicals mentioned therein is aryl or aralkyl and is monosubstituted to trisubstituted in the aromatic part by halogen.

The process according to the invention is carried out in the presence of one or more organic sulphur compounds of the formula (IV). Examples of such compounds are bis-(2-hydroxyethyl) sulphide, bis-(2-hydroxypropyl) sulphide, thiodiacetic acid, thiodipropionic acid and other similarly constructed compounds, their alkali metal salts and their lower esters (for example their dimethyl esters), thioanisole, diphenyl sulphide, dithiane, thioxane, thiophene, dimethyl sulphoxide, methyl ethyl sulphoxide or diethyl sulphoxide. The organic sulphur compound is employed in an amount from 0.002–0.5 parts by weight, preferably 0.01–0.25 parts by weight, per part by weight of catalyst. In a preferred manner, an organic sulphur compound of the formula $$R^{15}-S(=O)_n-R^{16} \qquad (IX)$$

is employed in which $R^{15}$ and $R^{16}$ independently of one another denote straightchain or branched $C-C_{12}$-alkyl, hydroxy-$C_2-C_{12}$-alkyl or carboxy-$C_1-C_{12}$-alkyl, where $R^{16}$ additionally may denote $CO-C_1-C_6$-alkyl and n assumes the value 0 or 1.

In a particularly preferred manner, bis-(2-hydroxyethyl) sulphide is employed.

The addition of the organic sulphur compound is carried out together with the catalyst, before the addition or after the addition of the catalyst. If the catalyst is re-used repeatedly, the organic sulphur compound in general only needs to be added to the catalyst or to the reaction mixture on the first use. The catalyst then retains its high specific activity together with a high yield even after repeated use many times or in a continuous procedure. However, a subsequent addition of the organic sulphur compound is possible, but usually only necessary, if fresh catalyst is added in place of somewhat spent or exhausted catalyst.

Hydrogenation catalysts employed according to the invention are Ni-containing and/or Co-containing, such as Ni or Co on supports, Ni or Co in the form of elemental Ni(Co) sponge, Ni-oxide, Co-oxide, Raney nickel, Raney cobalt or others. Supports are, for example, $SiO_2$, $Al_2O_3$, pumice, carbon and other supports known to those skilled in the art. However, in a preferred manner Raney catalysts, such as Raney nickel, Raney cobalt, Raney nickeliron, Raney nickel-cobalt or Raney nickel-iron-cobalt in anhydrous or even water-moist or solvent-moist form are employed. The Ni- and Co-containing catalysts can also be employed together.

The Ni-containing and/or Co-containing catalyst is employed in an amount of 1–25% by weight, preferably 2.5–12.5% by weight, relative to the substrate to be hydrogenated.

In a particularly preferred manner, Ni-containing Raney catalysts are employed.

The reaction medium employed can be alcohols, such as methanol, ethanol, isopropanol, butanol, aliphatic or aromatic hydrocarbons, such as toluene, xylene, cyclohexane, isooctane and the like, ethers, such as tetrahydrofuran, such as ethyl acetate and finally the reaction product itself, if it is liquid at the reaction temperature. A proportion of water (for example up to 20% by weight of the total reaction medium) does not interfere, especially if the reaction medium is miscible with water.

The hydrogenation is carried out at 30°–250° C, preferably at 50°–150° C, and an $H_2$ pressure of 5–200 bar, preferably 50–150 bar.

In general, the process according to the invention is carried out so that the starting material (hemiaminal, aminal or azomethine), the reaction medium, the catalyst and the organic sulphur compound are initially introduced into a hydrogenation autoclave and after closing the reactor the air is displaced with nitrogen and then the nitrogen with hydrogen. After completion of the reaction, the reaction vessel is initially depressurized and emptied; the catalyst is filtered off and may be re-used without a new addition of organic sulphur compounds. Otherwise, the working up is carried out in a manner known to those skilled in the art.

The process can be carried out batchwise and continuously, for example in a pressure tube having an attached separator and pressure release.

The process can furthermore be applied to the pure reaction products mentioned and to reaction mixtures in which hemiaminals, aminals or azomethines are prepared as such reaction products.

In a preferred manner, reaction mixtures in which such reaction products are prepared are used, the resulting reaction products being simultaneously hydrogenated in the manner according to the invention.

In a furthermore preferred manner, reaction mixtures are employed in which aldimines of the formula $$R^{31}-CH=NH \tag{X}$$

in which $R^{31}$ has the abovementioned meaning, are prepared by partial hydrogenation of the underlying nitriles, the aldimines simultaneously being further hydrogenated in a manner according to the invention. The partial hydrogenation of the nitriles is also carried out by means of the Ni-containing and/or Co-containing catalyst employed according to the invention in the presence of the organic sulphur compounds of the formula (IV).

It is surprising that, by means of the additional use of the organic sulphur compounds as modification agents for which in other cases a deactivation is observed, the described hydrogenation occurs more selectively, reproducibly and above all more completely than without this addition; the hydrogenation activity is therefore completely retained. The catalysts have a high stability. Damage to the Ni-containing and/or Co-containing catalysts by undesired by-products is not observed, as a result of which the frequent re-use described is possible. Furthermore, the use of very low reaction temperatures which make extremely long reaction times necessary is avoided. The substantial avoidance of undesired by-products not only increases the yield but also simplifies subsequent purification operations somewhat.

EXAMPLES (The examples are not optimized; a further increase in the yields and selectivities is therefore conceivable and probable)

EXAMPLE 1

α-(p-Chlorophenyl)-ethylamine

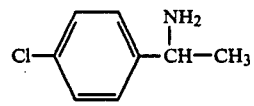

385 g (2.5 mol) of p-chloroacetophenone, 1125 ml of methanol, 3.8 g of bis-(2-hydroxyethyl) sulphide and also 12.5 g of ammonium acetate and 25 g of Raney nickel were initially introduced into a 3 liter stirred autoclave. After displacing the air with nitrogen and addition of 750 ml of liquid ammonia, the autoclave was pressurized with hydrogen up to a pressure of 80 bar and heated to 120° C. with stirring. After reaching this temperature, the pressure was increased to 120 bar and the consumption was compensated by further addition of hydrogen.

After the hydrogen uptake was complete in about 2 hours, the mixture was stirred further for another hour under the reaction conditions indicated, then cooled to room temperature and depressurization to atmospheric pressure.

The catalyst was filtered off and the methanol was distilled off. 388 g of crude product were obtained as a residue which contained, according to gas chromatographic analysis 90% of α-(p-chlorophenyl)-ethylamine
5% of α-phenethylamine
4.5% of α-(p-chlorophenyl)-ethanol and
0.5% of p-chloroacetophenone (educt).

For purification, the crude product was dissolved in 400 ml of toluene and washed with 100 ml of 20% strength sodium hydroxide solution. The toluene solution was concentrated and the residue was distilled through a packed column. 316.4 g (74% of theoretical yield) of the desired α-(p-chlorophenyl)-ethylamine were obtained as the main fraction having a boiling point of 115°–117° C./25 mbar and a purity of 98.7%.

EXAMPLE 2

α-(p-Chloropneny)-ethylamine

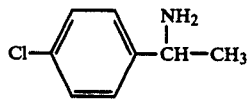

The reductive amination described under Example 1 was repeated, dimethyl sulphoxide being employed in the same amount instead of bis-(2-hydroxyethyl) sulphide.

After separating off the catalyst and the solvent, 386 g of the crude reaction product were obtained which according to gas chromatographic analysis contained
88.5% of α-(p-chlorophenyl)-ethylamine
5.5% of α-phenethylamine
4.5% of α-(p-chlorophenyl)-ethanol
1.0% of p-chloroacetophenone (educt).

EXAMPLE 3 (for comparison)

If the reductive amination described in Examples 1 and 2 was carried out without addition of one of the sulphur compounds, 384 g of a crude product was obtained after separating off the catalyst which according to gas chromatographic analysis contained
- 69% of α-(p-chlorophenyl)-ethylamine
- 26% of α-phenethylamine and
- 4% of α-(p-chlorophenyl)-ethanol.

EXAMPLE 4

N-Methyl-α-(p-chlorophenyl)-ethylamine

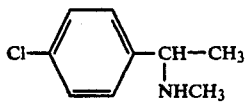

154 g of p-chloroacetophenone, 450 ml of methanol, 20 g of Raney nickel and 2 g of bis-(2-hydroxyethyl) sulphide were initially introduced into a 1.3 l stirred autoclave. After displacing the air with hydrogen and addition of 50 ml of liquid methylamine, the autoclave was pressurized with hydrogen up to a pressure of 80 bar and heated to 100° C. with stirring The pressure was adjusted to 140 bar and the consumption was compensated by further addition of hydrogen. The temperature was kept at 100° C. for another hour after the end of $H_2$ uptake.

After cooling and depressurizing, the catalyst was filtered off and the reaction solution was evaporated.

170 g of crude product were obtained which according to gas chromatographic analysis contained
- 86% of N-methyl-α-(p-chlorophenyl)-ethylamine
- 5.5% of α-(p-chlorophenyl)-ethanol
- 6 5% of N-methyl-α-phenethylamine
- 2% of unidentified by-products.

EXAMPLE 5

3-chloro-N-isopropyl-aniline

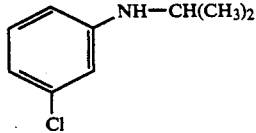

116 g of acetone, 255 g of 3-chloroaniline, 500 ml of methanol, 20 g of Raney nickel and 2 g of bis-(2-hydroxyethyl) sulphide were initially introduced into a 1.3 l stirred autoclave. After displacing the air with nitrogen, the autoclave was pressurized with hydrogen up to a pressure of 80 bar and heated to 120° C. with stirring. The pressure was adjusted to 150 bar and the consumption was compensated by further addition of hydrogen. The temperature was kept at 120° C. for another hour after the end of $H_2$ uptake.

After cooling and depressurizing, the catalyst was filtered off and the reaction solution was evaporated.

The 308 g of crude product thus obtained contained, according to gas chromatographic analysis:
- 77% of 3-chloro-N-isopropyl-aniline
- 12% of N-isopropyl-aniline
- 7% of 3-chloroaniline
- 4% of unidentified by-products.

EXAMPLE 6

4-chloro-N-isopropyl-aniline

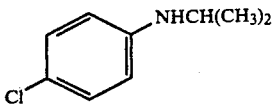

232 g of acetone, 255 g of 4-chloroaniline, 300 ml of ethanol, 25 g of Raney nickel-iron and 2.5 g of bis-(2-hydroxyethyl) sulphide were initially introduced into a 1.3 l stirred autoclave. After displacing the air with nitrogen, the autoclave was pressurized with hydrogen up to a pressure of 60 bar and heated to 100° C. with stirring. The pressure was adjusted to 100 bar and the consumption was compensated by further addition of hydrogen. The temperature was kept at 100° C. for another hour after the end of $H_2$ uptake.

After cooling and depressurizing, the catalyst was filtered off and the reaction solution was evaporated.

The 310 g of crude product thus obtained contained, according to gas chromatographic analysis:
- 82% of 4-chloro-N-isopropyl-aniline
- 8.5% of N-isopropyl-aniline
- 6.5% of 4-chloroaniline and
- 3% of unidentified by-products.

EXAMPLE 7

3-chloro-N-nepentyl-aniline

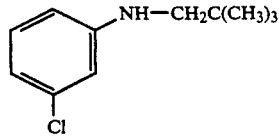

172 g of pivalaldehyde, 255 g of 3-chloroaniline, 400 ml of tetrahydrofuran, 25 g of Raney nickel and 2.5 g of bis-(2-hydroxyethyl) sulphide were initially introduced into a 1.3 l stirred autoclave After displacing the air with nitrogen, the autoclave was pressurized with hydrogen up to a pressure of 80 bar and heated to 120° C. with stirring The pressure was adjusted to 140 bar and the consumption was compensated by further addition of hydrogen. The temperature was kept at 120° C. for another hour after the end of $H_2$ uptake.

After cooling and depressurizing, the catalyst was filtered off and the reaction solution was evaporated.

The 355 g of crude product thus obtained contained, according to gas chromatographic analysis
- 76% of 3-chloro-N-neopentyl-aniline
- 7.5% of N-neopentyl-aniline
- 12.5% of 3-chloroaniline and
- 4% of unidentified by-products.

EXAMPLE 8

3-Amino-5-(4-chlorophenyl)-2,2-dimethyl-pentane

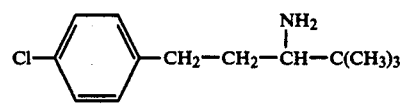

168 g of 5-(4-chlorophenyl)-2,2-dimethyl-pentan-3-one, 160 ml of methanol, 20 g of Raney nickel, 1 g of bis-(2-hydroxyethyl) sulphide and 5 g of ammonium acetate are initially introduced into a 1.3 l stirred autoclave. After displacing the air with nitrogen and addition of 500 ml of liquid ammonia, the autoclave was pressurized with hydrogen up to a pressure of 90 bar and heated to 125° C. with stirring. The pressure was adjusted to 120 bar and the consumption was compensated by further addition of hydrogen. The temperature was kept at 125° C. for another hour after the end of $H_2$ uptake.

After cooling and depressurizing, the catalyst was filtered off and the reaction solution was evaporated.

The 172 g of crude product thus obtained contained, according to gas chromatographic analysis:

73% of 3-amino-5-(4-chlorophenyl)-2,2-dimethyl pentane
5% of 5-(4-chlorophenyl)-2,2-dimethyl-3-hydroxy pentane
0.5% of dechlorinated compounds
20% of educt.

EXAMPLE 9

2-Amino-4-chloro-benzylamine

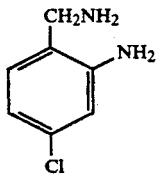

152 g (1 mol) of 2-amino-4-chloro-benzonitrile, 400 ml of isopropanol, 15% of Raney nickel and 1 g of bis-(2-hydroxyethyl) sulphide were initially introduced into a 1.3 l stirred autoclave. After displacing the air with nitrogen and addition of 150 ml of liquid ammonia, the autoclave was pressurized with hydrogen up to a pressure of 80 bar and heated to 80° C. with stirring. The pressure was adjusted to 140 bar and the consumption was compensated by further addition of hydrogen. The temperature was kept at 80° C. for another hour after the end of $H_2$ uptake.

After cooling and depressurizing, the catalyst was filtered off and the reaction solution was evaporated.

The 153 g of crude product thus obtained contained, according to gas chromatographic and mass spectroscopic (GC-MS coupling) analysis:

98.5% of 2-amino-4-chloro-benzylamine and
<0.1% of dechlorination products.

EXAMPLE 10

4-Amino-2,5-dichloro-benzylamine

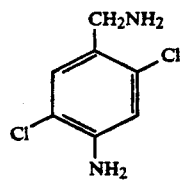

94 g (0.5 mol) of 4-amino-2,5-dichloro-benzonitrile, 300 ml of methanol, 10 g of Raney nickel-iron and 1 g of bis-(2-hydroxyethyl) sulphide were initially introduced into a 1.3 l stirred autoclave. After displacing the air with nitrogen and addition of 200 ml of liquid ammonia, the autoclave was pressurized with hydrogen up to a pressure of 60 bar and heated to 70° C. with stirring. The pressure was adjusted to 100 bar and the consumption was compensated by further addition of hydrogen.

The temperature was kept at 70° C. for another hour after the end of $H_2$ uptake.

After cooling and depressurizing, the catalyst was filtered off and the reaction solution was evaporated.

The 95 g of crude product thus obtained contained, according to gas chromatographic and MS analysis:

95% of 4-amino-2,5-dichloro-benzylamine.

EXAMPLE 11

4-Chlorophenyl-phenyl-methylamine

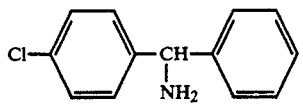

162 g of 4-chlorobenzophenone, 450 ml of methanol, 10 g of Raney nickel, 1.5 g of bis-(2-hydroxyethyl) sulphide and 5 g of ammonium acetate were initially introduced into a 1.3 l stirred autoclave. After displacing the air with nitrogen and addition of 300 ml of liquid ammonia, the autoclave was pressurized with hydrogen up to a pressure of 80 bar and heated to 125° C. with stirring. The pressure was adjusted to 120 bar and the consumption was compensated by further addition of hydrogen. The temperature was kept at 125° C. for another hour after the end of $H_2$ uptake.

After cooling and depressurizing, the catalyst was filtered off and the reaction solution was evaporated.

The 160 g of crude product thus obtained contained, according to gas chromatographic and mass spectroscopic analysis:

88% of (4-chlorophenyl)-phenyl-methyl-amine
3% of diphenyl-methylamine
2.4% of (4-chlorophenyl)-phenyl-methane
3.4% of bis-[(4-chlorophenyl)-phenylmethyl]amine
1.3% of educt

EXAMPLE 12

1-Amino-2-(4-chlorophenyl)-ethane

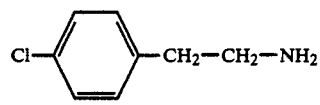

100 g of 4-chlorobenzyl cyanide, 100 g of methanol, 5.0 g of water-moist Raney nickel and 0.75 g of bis-(2-hydroxyethyl) sulphide were initially introduced into a 0.7 l stirred autoclave. After displacing the air with nitrogen and addition of 30 g of ammonia, the autoclave was pressurized with hydrogen up to a pressure of 100 bar and heated to 130° C. with stirring. As soon as uptake of hydrogen was detected, the pressure was adjusted to 150 bar and the consumption was compensated by further addition of hydrogen. The temperature was kept at 130° C. for a further 30 minutes after the completion of $H_2$ uptake.

After cooling and depressurizing, the catalyst was filtered off. The reaction solution contained according to gas chromatographic analysis:

0.77% of unknown substances (4 peaks)
99.01% of 1-amino-2-(p-chlorophenyl)ethane
0.22% of unknown substances (3 peaks)

EXAMPLE 13 (for comparison)

The procedure was as in Example 12, but without bis-(2-hydroxyethyl) sulphide. The gas chromatographic analysis gave:
0.71% of unknown substances (4 peaks)
91.67% of 1-amino-2-(p-chlorophenyl)ethane
0.03% of unknown substance
1.96% of unknown substance
5.58% of unknown substance
0.05% of unknown substance (total of 4 peaks)

EXAMPLE 14 o-Chlorobenzylamine

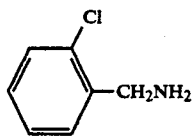

140.6 g of o-chlorobenzaldehyde, 100 g of methanol, 8.4 9 of methanol-moist Raney nickel and 0.2 g of bis-(2-hydroxyethyl) sulphide were initially introduced into a 0.7 l stirred autoclave. After displacing the air with nitrogen and addition of 102 g of ammonia, the autoclave was pressurized with nitrogen up to a pressure of 90 bar and heated to 100° C. with stirring. The pressure was again adjusted to 90 bar and the consumption thus compensated by further addition of hydrogen. The temperature was kept at 100° C. for another hour after the completion of $H_2$ uptake.

After cooling and depressurizing, the catalyst was filtered off. The reaction solution contained according to gas chromatographic analysis:
0.9% of benzylamine
90.5% of o-chlorobenzylamine
6.8% of o-chlorobenzyl alcohol

EXAMPLE 15 (for comparison)

The procedure was as in Example 14, but without bis-(2-hydroxyethyl) sulphide. The gas chromatographic analysis gave:
3.6% of benzylamine
80.2% of o-chlorobenzylamine
13.8% of o-chlorobenzyl alcohol

EXAMPLE 16

α-(p-Chlorophenyl)-N,N-dimethyl-ethylamine

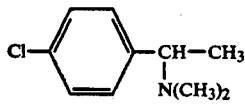

15.5 g (0.1 mol) of α-(p-chlorophenyl)-ethylamine, 100 ml of methanol, 13.5 g of a 50% strength methanolic formaldehyde solution (0.22 mol), 2 g of Raney nickel and 0.15 g of bis-(2-hydroxyethyl) sulphide were initially introduced into a 0.3 l stirred autoclave. After displacing the air with nitrogen, the autoclave was pressurized with hydrogen up to a pressure of 80 bar and heated to 110° C. with stirring. The pressure was adjusted to 160 bar and the consumption was compensated by further addition of hydrogen. The temperature was kept at 110° C. for another hour after the end of $H_2$ uptake.

After cooling and depressurizing, the catalyst was filtered off and the reaction solution was evaporated.

The 16.9 g of crude product thus obtained contained, according to gas chromatographic and mass spectroscopic analysis:
91.8% of α-(p-chlorophenyl)-N,N-dimethyl-ethyl amine,
1.5% of α-(p-chlorophenyl)-N-methyl-ethylamine,
5.7% of N,N-dimethyl-α-phenyl-ethylamine and
1% of unidentified by-products.

EXAMPLE 17

α-(3,4-dichlorophenyl)-ethylamine

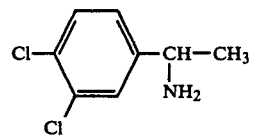

94.5 g of 3,4-dichloroacetophenone, 225 ml of methanol, 2.5 g of ammonium acetate, 5 g of Raney nickel and 1 g of bis-(2-hydroxyethyl) sulphide were initially introduced into a 0.7 l stirred autoclave. After displacing the air with nitrogen and addition of 15 ml of liquid ammonia, the autoclave was pressurized with hydrogen up to a pressure of 80 bar and heated to 125° C. with stirring. The pressure was adjusted to 120 bar and the consumption was compensated by further addition of hydrogen. The temperature was kept at 125° C. for another hour after the end of $H_2$ uptake.

After cooling and depressurizing, the catalyst was filtered off and the reaction solution was evaporated.

The 93 g of crude product thus obtained contained, according to gas chromatographic analysis:
87% of α-(3,4-dichlorophenyl)-ethylamine,
3% of α-phenethylamine,
4.5% of α-(3,4-dichlorophenyl)-ethanol and
5.5% of unidentified by-products.

What is claimed is:

1. A process for the preparation of amines of the formula

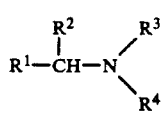

in which
R[1], R[2] and R[3] independently of one another denote hydrogen, straight-chain or branched $C_1$–$C_{12}$-alkyl, $C_3$–$C_8$-cycloalkyl, $C_6$–$C_{12}$-aryl or $C_7$–$C_{10}$-aralkyl and R[4] represents hydrogen, straight-chain or branched $C_1$–$C_{20}$-alkyl, $C_6$–$C_{12}$-aryl, $C_3$–$C_8$-cycloalkyl or $C_7$–$C_{10}$-aralkyl, where at least one of the radicals R[1] to R[4] represents aryl or aralkyl which are monosubstituted to trisubstituted by halogen in the aromatic moiety, by catalytic hydrogenation of reaction products of oxo compounds of the formula

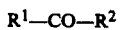

and nitrogen compounds of the formula

with the abovementioned meanings for $R^1$ to $R^4$, which is characterized in that a Ni-containing and-/or Co-containing catalyst is employed and that the reaction is carried out in the presence of organic sulphur compounds of the formula $$R^5-S(=O)_n-R^6$$

which $R^5$ and $R^6$ independently of one another denote straight-chain or branched $C_1$-$C_{12}$-alkyl, hydroxy-$C_2$-$C_{12}$-alkyl, carboxy-$C_1$-$C_{12}$-alkyl or phenyl and furthermore $R^5$ and $R^6$ together may represent $-CH=CH-CH=CH-$, $-(CH_2)_4-$, $-(CH_2)_5-$, $-(CH_2)_5-$, $-(CH_2)_2-S-(CH_2)_2-$ or $-(CH_2)_2-O-(CH_2)_2-$ $R^6$ additionally may denote hydrogen or $CO$-$C_1$-$C_{12}$-alkyl and n assumes the value 0 or 1.

2. The process according to claim 1, characterized in that organic sulphur compounds of the formula $$R^{15}-S(=O)_n-R^{16}$$

are employed in which $R^{15}$ and $R^{16}$ independently of one another denot straight-chain or branched $C_2$-$C_{12}$-alkyl, hydroxy-$C_2$-$C_{12}$-alkyl or carboxy-$C_1$¤$C_{12}$-alkyl, where $R^{16}$ additionally may denote $CO$-$C_1$-$C_6$-alkyl and n assumes the value 0 or 1.

3. The process according to claim 2, characterized in that bis-(2-hydroxyethyl) sulphide is employed.

4. The process according to claim 1, characterized in that Raney nickel, Raney cobalt, Raney nickel-iron, Raney nickel-cobalt or Raney nickel-iron-cobalt are employed as catalyst.

5. The process according to claim 1, characterized in that reaction mixtures in which the reaction products of the oxo compounds and the nitrogen compounds are prepared are employed.

6. The process according to claim 1, characterized in that reaction mixtures are employed in which azomethines of the formula $$R^{31}-CH=NH$$

in which $R^1$ denotes $C_1$-$C_{12}$-alkyl, $C_3$-$C_8$-cycloalkyl, $C_6$-$C_{12}$-aryl or $C_7$-$C_{10}$-aralkyl, are prepared by partial hydrogenation of the underlying nitriles.

7. The process according to claim 1, characterized in that, as oxo compounds, those of the formula $$R^{11}-CO-R^{12}$$

are employed in which $R^{11}$ denotes hydrogen, straight-chain or branched $C_1$-$C_{12}$-alkyl, $C_3$-$C_6$-cycloalkyl, phenyl, benzyl or phenyl-ethyl and $R^{12}$ represents hydrogen, straight-chain or branched $C_1$-$C_4$-alkyl or phenyl.

8. The process according to claim 7, characterized in that, as oxo compounds, those of the formula $$R^{21}-CO-R^{22}$$

are employed in which $R^{21}$ denotes hydrogen, straight-chain or branched $C_1$-$C_4$-alkyl, $C_5$-$C_6$-cycloalkyl, phenyl, benzyl or phenylethyl and $R^{22}$ represents hydrogen, methyl or ethyl.

9. The process according to claim 1, characterized in that, as nitrogen compounds, those of the formula $$R^{13}-NH-R^{14}$$

are employed in which $R^{13}$ denotes hydrogen, straight-chain or branched $C_1$-$C_8$-alkyl, $C_3$-$C_6$-cycloalkyl, phenyl or benzyl and $R^{14}$ represents hydrogen, straight-chain or branched $C_1$-$C_4$-alkyl or benzyl.

10. The process according to claim 9, characterized in that, as nitrogen compounds, those of the formula $$R^{23}-NH-R^{24}$$

are employed in which $R^{23}$ denotes hydrogen, straight-chain or branched $C_1$-$C_4$-alkyl, $C_5$-$C_6$-cycloalkyl, phenyl or benzyl and $R^{24}$ represnts hydrogen, methyl or ethyl.

11. The process according to claim 1, characterized in that the organic sulphur compound is employed in an amount from 0.002-0.5 parts by weight per part by weight of catalyst.

12. The process according to claim 11, characterized in that the organic sulphur compound is employed in an amount from 0.01-0.25 parts by weight per part by weight of catalyst.

13. The process according to claim 1, characterized in that the Ni-containing and/or Co-containing catalyst is employed in an amount of 1-25% by weight, relative to the substrate to be hydrogenated.

14. The process according to claim 13, characterized in that the Ni-containing and/or Co-containing catalyst is employed in an amount of 2.5-12.5% by weight, relative to the substrate to be hydrogenated.

15. The process according to claim 1, characterized in that it is carried out at 30°-250° C.

16. The process according to claim 15, characterized in that it is carried out at 50°-150° C.

17. The process according to claim 1, characterized in that it is carried out at an $H_2$-pressure of 5-200 bar.

18. The process according to claim 17, characterized in that it is carried out at an $H_2$-pressure of 10-150 bar.

* * * * *